United States Patent [19]

Kosuth

[11] Patent Number: 5,178,021

[45] Date of Patent: Jan. 12, 1993

[54] FLUID SAMPLE BAGS WITH INTERNAL SPACING ELEMENT

[75] Inventor: John M. Kosuth, Washington, Mich.

[73] Assignee: Bagtech, Inc., Hazel Park, Mich.

[21] Appl. No.: 869,479

[22] Filed: Apr. 15, 1992

Related U.S. Application Data

[63] Continuation of Ser. No. 661,417, Feb. 26, 1991, abandoned.

[51] Int. Cl.⁵ .............................................. G01N 1/10
[52] U.S. Cl. .................. 73/864.62; 222/105; 383/33
[58] Field of Search ............... 73/864.62; 222/92, 105, 222/106, 107; 383/33, 35

[56] References Cited

U.S. PATENT DOCUMENTS

| | | | |
|---|---|---|---|
| 4,148,416 | 4/1979 | Gunn-Smith | 222/94 |
| 4,524,458 | 6/1985 | Pongrass et al. | 383/33 |
| 4,601,410 | 7/1986 | Bond | 383/33 X |

Primary Examiner—Jerry W. Myracle
Attorney, Agent, or Firm—Barnes, Kisselle, Raisch, Choate, Whittemore & Hulbert

[57] ABSTRACT

There is provided a fluid sample bag for use in testing automotive exhaust samples and the like. The bag can be sealed and formed of a material which is flexible and impermeable to gases. A fitting is sealingly connected to the bag for filling and evacuating the bag. A spacing element is carried on the fitting and disposed in the interior of the bag, extending substantially throughout the interior of the bag and closely adjacent the perimeter of the bag when the bag is collapsed. The spacing element is a sheet of mesh material or other grid-like array that forms a plurality of passages which provide for fluid flow between the fitting and substantially everywhere within the bag when the bag collapses on the spacing element. The spacing element is polyester, stainless steel or the like, depending on the sample application, so as to be inert with the sample. The mest opening size is selected to prevent the bag from collapsing entirely upon itself in a manner that would otherwise form pockets of the sample isolated from the fitting.

23 Claims, 2 Drawing Sheets 5,178,021

FLUID SAMPLE BAGS WITH INTERNAL SPACING ELEMENT

This is a continuation of copending application Ser. No. 07/661,417 filed on Feb. 26, 1991, now abandoned.

FIELD OF THE INVENTION

This invention relates to fluid sample bags and in particular to an internal spacing element that enhances fluid flow when a sample is introduced into and extracted from the bag.

BACKGROUND AND SUMMARY OF THE INVENTION

Fluid sample bags are used in a variety of applications to obtain gaseous and liquid fluid samples, for example in testing automotive exhaust gases. Typically, a fluid sample bag comprises a flexible bag which is sealed and impermeable to prevent leakage and loss of the sample from the bag and protect against contamination of the sample. It is particularly important that the bags be impermeable to gases where gaseous fluid samples are taken. Typically, the fluid sample bag includes a fitting to introduce a measured quantity sample into the bag and then to remove the sample from the bag.

The sample is removed for testing to determine whether certain constituents are present within the sample and to quantify the presence of the constituents, typically contaminants in the case of automotive exhaust gases. In many cases the constituents are present in very small quantities, e.g., parts per million. Therefore, if the measured sample is not completely removed from the bag, constituents may be left in the bag and remain undetected. In addition, if it is desired to reuse the bag repeatedly, a given sample from the bag must be completely evacuated so that it does not contaminate a subsequent sample.

A typical prior art bag B, as shown in FIGS. 1 and 1A, is assembled with a fitting F and flexible tubing T inside the bag. The bag is sold assembled with the fitting F and tubing T. Tubing T is intended to serve as a manifold to introduce and to extract the sample.

However, as shown in FIGS. 1 and 1A, prior art bags B having flexible tubing T may form pockets P of entrapped gas when the bag is evacuated. This occurs because the top and bottom of the bag B can collapse onto itself, sealing off pockets P during evacuation.

Objects, features and advantages of this invention are to provide a fluid sample bag which, as contrasted to prior art bags, is reliable and operates effectively to provide accurate and repeatable fluid sampling. According to the present invention, the prior art tubing inside the bag is replaced with a spacing element that enhances fluid flow, facilitates drawing a sample from the bag, and restricts collapsing of the bag onto itself and thus prevents the formation of isolated pockets of fluid sample and insures substantially complete evacuation of a sample from the bag.

These and other advantages and features of the invention will be apparent from the following detailed description and claims.

DETAILED DESCRIPTION OF THE INVENTION

Figure 1:
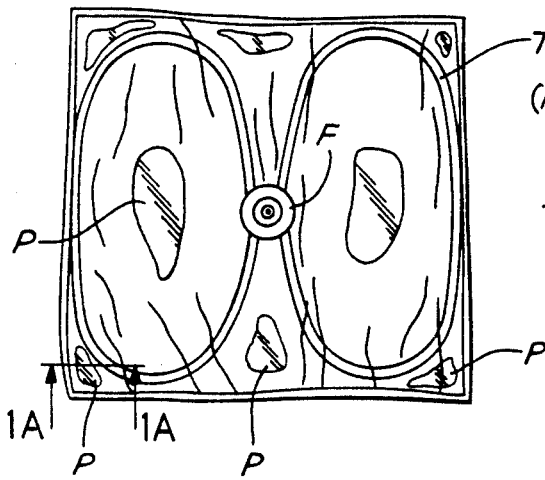
FIG. 1 is a top view of a prior art fluid sample bag.

Referring to the embodiment shown in FIGS. 2–6, a fluid sample bag 10 comprises a bag, per se, 12 which is formed by a top sheet 14 and a bottom sheet 16 sealed together at 18 adjacent to and around the entire outer perimeter to provide a collapsible interior chamber 22. Bag 12 has a rectangular geometry and may have the same length and width dimension as the prior art bag B shown in FIG. 1. A fitting 20 is sealably mounted on top sheet 14 to connect to the bag 12 to provide fluid communication from the interior chamber 22 to the exterior of the bag 12 at 24. Disposed within chamber 22 of bag 12 is a spacing element 26 which enhances fluid flow to and from the chamber 22 via fitting 20. The spacing element 26 extends substantially throughout the interior chamber 22 of bag 12 and has its perimeter closely adjacent seal 18 of bag 12, leaving a small unoccupied peripheral border 19.

Fitting 20 comprises two disc-shaped flange members 28, 30 positioned within the interior 22 of the bag 12 which support the spacing element 26 sandwiched between the flanges. The base flange member 28 includes a tubular member 32 which extends through a hole 33 in the spacing element 26, a hole 35 in flange 28 and a hole 37 in sheet 14 to provide a passage 34 from the interior chamber 22 of the bag 12 to the exterior 24 of the bag 12. The tubular member 32 also has four holes 36 opening radially of the tubular member 32 immediately adjacent flange 30 to provide fluid communication from the interior chamber 22 through holes 36 and passage 34. The tubular member 32 has external threads 40 which engage the internal threads 42 of a nut 44. As the nut 44 is secured to the tubular member 32, compressible O-rings 46a and 46c are clamped together with a rigid washer 46(b) to provide sealing engagement between the fitting 20 and the bag 12 so that fluid may only enter the bag 12 and be evacuated from the bag 12 through the fitting 20. In use, the sample is stored in bag 12 by a cap (not shown) screwed on fitting 20.

Figure 5:
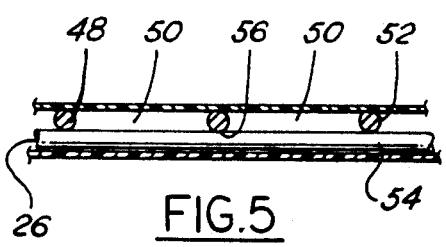
Figure 6:
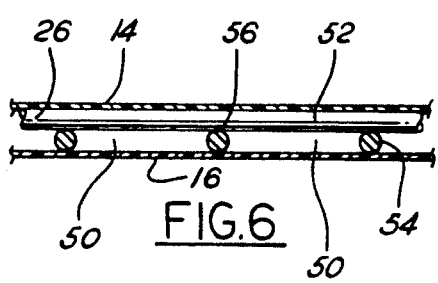

The spacing element 26 shown in FIGS. 2–6 comprises a flat sheet of flexible mesh material providing an integral, flexible, grid-like array or mesh of filamentary strips 48. Strips 48 are arranged in a first group of strips 52, disposed in spaced-apart, parallel relation to one another, and a second group of strips 54, also disposed in spaced-apart, parallel relation to one another. The first group of strips 52 are laid over the second group of strips 54 so that strips 52 intersect and are generally perpendicular to strips 54. Strips 52 are attached to strips 54 at points of intersection 56 (FIGS. 5 and 6). This mesh geometry forms a plurality of channel passages 50 in the space between adjacent strips 52 and also in the space between strips 54. With strips 52, 54 disposed generally diagonally of chamber 22, channels 50 provide communication between holes 36 and substantially throughout chamber 22. For example, as viewed in FIG. 3, holes 36 are connected directly with the upper left and lower right corners by channels 50 between the lower strips 54 and with the lower left and upper right corners by channels 50 between the upper strips 52. Because the upper channels 50 between strips 52 also communicate with the lower channels 50 between strips 54, and vice versa, the channels provide communication with holes 36 substantially everywhere within chamber 22.

Figure 1A:
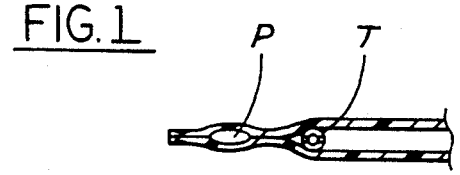
FIG. 1A is a fragmentary sectional view taken on the line 1A—1A of FIG. 1.
Figure 2:
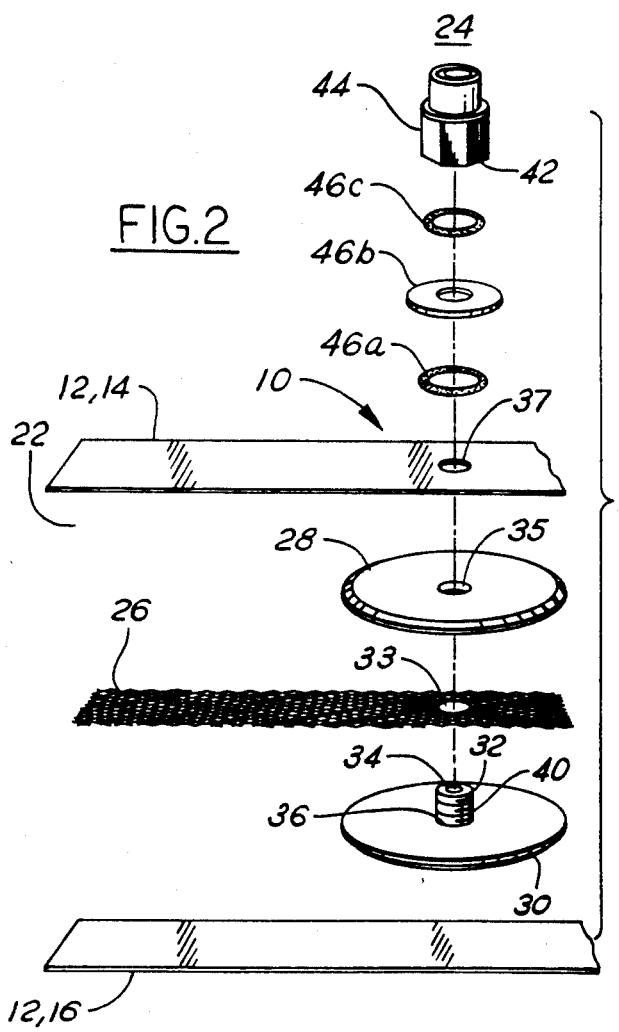
FIG. 2 is an exploded, fragmentary view of a fluid sample bag embodying the invention.
Figure 4:
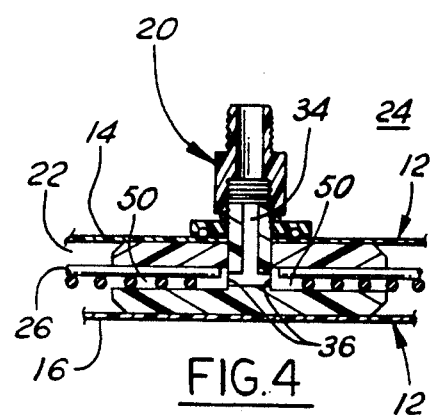
FIGS. 4, 5 and 6 are fragmentary sectional views taken on the lines 4—4, 5—5 and 6—6, respectively, of FIG. 3.

According to one important aspect of the present invention, the grid-like array of passages 50 not only provide communication between holes 36 and substantially everywhere within chamber 22, but the spacing element 26 prevents total collapsing of bag 12 on itself to form large pockets P that presented a drawback in the prior art shown in FIGS. 1 and 1A.

In one implementation of the embodiment being described, chamber 22 was approximately thirteen-and-a-half inches long and seven-and-a-half inches wide. The spacing element 26 extends to within about a quarter of an inch (border 19) of the peripheral seal 18. Border 19 accommodates dimensional changes as the bag inflates when a sample is introduced into chamber 22. Spacing element 26 was cut from a sheet of mesh material that is sold commercially as an aqua culture and marine netting manufactured and distributed by Naltex of Austin, Texas. This mesh material is made of polyester, which is relatively inert for many gas sampling applications. It is also relatively inexpensive and flexible, yet self-supporting. This particular polyester mesh was not a standard mesh size but had about three mesh openings per inch. Hence the dimension between adjacent strips 52 and between adjacent strips 54 was slightly over one quarter inch and the strips 52, 54 intersected at approximately 90°. The thickness of the spacing element 26 was between about 80 and 100 thousandths of an inch, depending on where the measurement is taken.

Although polyester mesh is relatively low in cost and suitable for some applications, it is important that the material be inert to the gas or other fluid being sampled so as not to contribute any contaminants to the sample and so as not to absorb any of the gas sample. Similarly, fitting 20 should be made of inert material such as Teflon (trademark of DuPont Corporation for its polytetrafluoroethylene) or stainless steel. The bag material is a thin plastic film which is typically a 2-mils-thick polyvinyl fluoride or polytetrafluoroethylene film material available from DuPont Corporation and sold under the respective trademarks "Tedlar" and "Teflon." With films of this thickness, the film does not stretch significantly for automotive emission testing applications.

Although spacing element 26 has been found useful for certain applications when made from the polyester mesh described hereinabove, other applications require a more expensive, more inert stainless steel mesh wherein the strips 52, 54 are stainless steel wires, secured together by resistance welding at the intersections, with a one-quarter-inch spacing between the wires and four openings per inch, a standard Number "4" mesh. Although this stainless steel mesh is also available commercially, the selection of a stainless steel mesh or a polyester mesh will depend upon the specific gas or other fluid for which the sampling bag is being used. With a polyester mesh, it is relatively easy to contour the exposed end tips 60 of strips 52, 54 so as to be smooth with no sharp edges which might pierce the bag. This contouring may be achieved by merely heating the tips 60 until they soften, without melting and running. With stainless steel, the tips 60 can be contoured by deburring.

It will be apparent that the effectiveness of the present invention is a function of several factors, including the strength, flexibility and thickness of the top and bottom sheets 14, 16, the dimensions of the strips 52, 54, the spacing between the strips, the angles and manner in which the strips intercept, the distance between the points of intersection, and the sampling parameters. In any event, the intersecting strips provide a tent-like arrangement which maintains the top and bottom of the bag in spaced-apart relation while the opening in the mesh provides a void space or cell with individual cells being interconnected to provide the passageways 50 in the manner described hereinabove. During the final stage of evacuation, the sheets will collapse toward and finally touch each other in the center of a cell without isolating the cell or otherwise forming an entrapped bubble or pocket of the sample. With the spacing element 26 constructed of a mesh, whether polyester or stainless steel, although a quarter-inch spacing has been used effectively, the present invention also contemplates spacing up to at least on the order of one-half inch, and possibly larger so long as isolated pockets are eliminated. However, spacing of one-quarter to one-half inch, or approximately two to four mesh openings per inch, is believed to be effective for many applications to sample automotive exhaust gases. Similarly, although commercially-available mesh of the type described has strips that intersect at an angle of about 90°, the angle of intersection is not necessarily required so long as the mesh provides channel passages that establish communication between holes 36 and substantially everywhere within the chamber 22.

Figure 3:
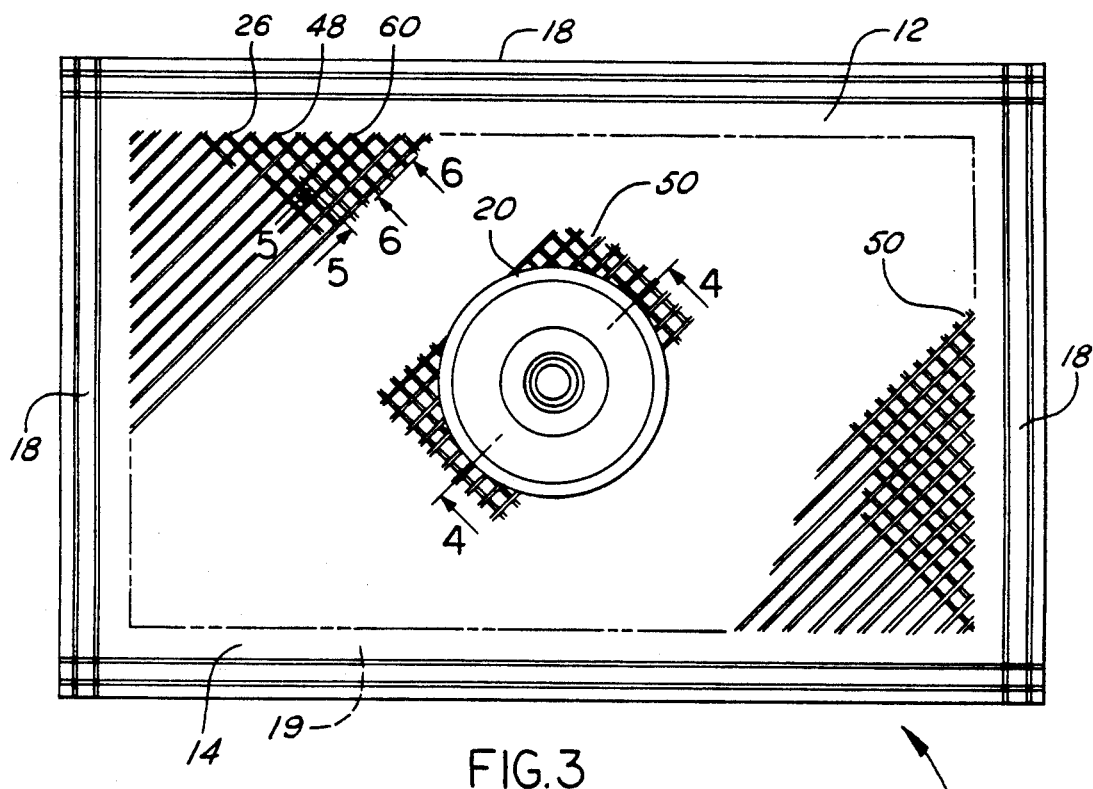
FIG. 3 is a top view of the fluid sample bag of the present invention with a fragmentary showing of a spacing element.

The fluid sample bag 12 can be easily and economically assembled by first cutting the top and bottom sheets 14, 16 to the desired rectangular dimensions and then cutting the spacing element 26 from a sheet of mesh material to the dimensions required to substantially fill chamber 20 with a small border 19. The tips 60 along the outer peripheral edges of spacing element 26 are then contoured to remove sharp edges and holes 33, 37 are cut in the spacing element 26 and the top sheet 14. The tubular member 32 on flange member 30 is then inserted through holes 33, 35, 37. Washer 46(b) and O-rings 46(a) and (c) are assembled on the projecting tubular member 32 and when nut 44 is tightened on member 34, the spacing element 26 is clamped between flange members 28 and 30 and the top sheet 14 is similarly clamped between flange member 28 and washer 46(b). With the spacing element 26 assembled on sheet 14, sheet 14 can then be assembled with the bottom sheet 16 and the two sheets sealed together around the entire perimeter thereof, as by heat sealing, to form chamber 22 with spacing element 26 assembled therein. As illustrated in FIG. 3, heat seal 18 is preferably a double heat seal, as contrasted to single heat seals typically used with prior art bags.

The sample bag 12, like the prior art sample bags shown in FIGS. 1 and 1A, is constructed so that new sample bags can be reconstructed by reusing some or all of the parts of the fitting and/or the spacing element. A new bag can be reconstructed by returning a used bag to the supplier who disassembles the old bag and merely replaces the top and bottom sheets, 14, 16 and, depending upon the application, either reuse or replace the spacing element 26 with a new element and either reuse or replace new O-rings 46(a) and (c).

Although particular embodiments of the spacing element 26 have been described with a specific mesh geometry, it will be apparent that other mesh arrangements can also be used to provide passages that establish a fluid communication between holes 36 and substantially everywhere within chamber 22 while preventing isolated pockets.

Figure 7:
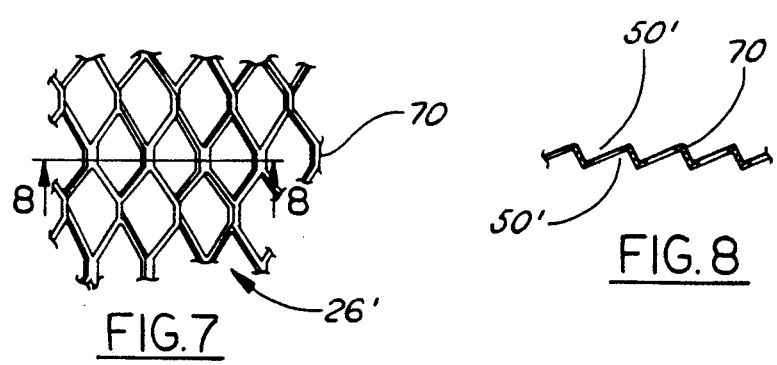
FIG. 7 is a fragmentary top view of a modification in the spacing element.
Figure 8:
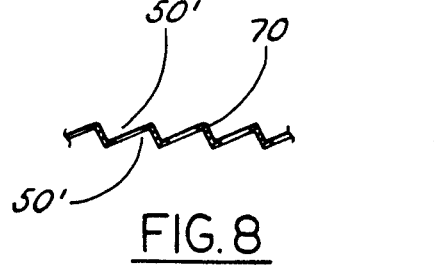
FIG. 8 is a sectional view taken on the line 8—8 of FIG. 7.

Referring to FIGS. 7 and 8, there is shown an alternative embodiment of the mesh used to form spacing element 26' that has been cut from a sheet of commercially available expanded metal 70 that forms channel passages 50'.

Figure 9:
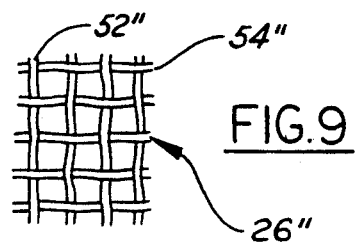
FIG. 9 is a top view of a further modification of the spacing element.

In a still further embodiment shown in FIG. 9, the spacing element 26" comprises a first group of strips 52" interwoven with a second group of strips 54" so that individual strips 52" alternatively cross over and then under the successive strips 54". It will be apparent that the thickness of the spacing element 26" at these cross-over points is twice the thickness of each strip so as to provide a series of undulating passages corresponding to passages 50 in FIGS. 3-6 that will establish fluid communication between holes 36 and substantially everywhere within chamber 22.

Although various arrangements of a mesh material have been described for spacing element 26, other mesh geometries and indeed other geometries of the spacing element are also contemplated by the present invention, so long as they provide effective fluid communication between the interior of chamber 20 and holes 36 while at the same time serving as a spacing element to prevent collapse of the bag in a manner that would otherwise form pockets which trap bubbles of the gas or other fluid.

Although specific embodiments of the present invention have been described hereinabove for purposes of illustration and not limitation, various other modifications and variations are contemplated by the present invention, the scope of which is set forth in the following claims.

I claim:

1. In a fluid sample bag of the type providing a sealed chamber formed by flexible sheet material impervious to fluids being sampled and a fitting on said bag to introduce a fluid sample into said chamber and extract said sample from said chamber, at least a portion of said bag being substantially flat in a collapsed condition when said sample is extracted from said chamber and being extendable to an inflated condition when said sample is introduced into said chamber, said bag having top and bottom walls when said bag is collapsed, the improvement comprising spacing means disposed between said top and bottom walls and extending substantially throughout said chamber for restricting said walls from collapsing on each other and for establishing fluid communication from said fitting substantially everywhere within said chamber when said bag is collapsed so that said sample can be substantially fully evacuated without forming pockets of said sample isolated from said fitting.

2. The fluid sample bag improvement set forth in claim 1 wherein said spacing means comprises a grid-like array of filamentary strips arranged and disposed to provide a plurality of passageways establishing fluid communication between said fitting and substantially everywhere within said chamber.

3. The sample bag improvement set forth in claim 2 wherein said spacing means comprises a sheet of mesh material forming said grid-like array.

4. The sample bag improvement set forth in claim 3 wherein said mesh material is an expanded material.

5. The sample bag improvement set forth in claim 3 wherein said mesh material is woven.

6. The sample bag improvement set forth in claim 3 wherein said mesh material has mesh openings in the range of about two to four mesh openings per inch.

7. The sample bag improvement set forth in claim 3 wherein said plurality of strips comprises a first group of strips disposed in spaced apart relation and a second group of strips disposed in spaced apart relation, said groups intersecting at points of intersection.

8. The sample bag improvement set forth in claim 7 wherein said first group is laid over said second group.

9. The sample bag improvement set forth in claim 7 wherein said first group and said second group are woven together with each respective strip of said first group alternatively crossing over and then under successive strips of said second group.

10. The sample bag improvement set forth in claim 3 wherein said mesh material is polyester.

11. The sample bag improvement set forth in claim 3 wherein said mesh material is stainless steel.

12. The sample bag improvement set forth in claim 2 wherein said spacing means is mounted on said fitting.

13. The sample bag improvement set forth in claim 12 wherein said fitting comprises a pair of flanges disposed inside said bag and said spacing means is clamped between said flanges with said passageways in fluid communication with said fitting.

14. The sample bag improvement set forth in claim 1 wherein said spacing means extends substantially throughout said chamber and terminates closely adjacent a perimeter of said chamber when said bag is flat to accommodate dimensional changes when said bag is inflated.

15. In a fluid sample bag of the type providing a sealed chamber formed by flexible sheet material impervious to fluids being sampled and a fitting on said bag to introduce a fluid sample into said chamber and extract said sample from said chamber, said bag having opposed wall surfaces engaging each other when said bag collapses as said sample is extracted from said chamber and disengaging from each other when said bag inflates as said sample is introduced into said chamber, the improvement comprising passageway means extending from said fitting substantially throughout said chamber when said bag collapses for establishing fluid communication from said fitting to substantially everywhere within said chamber so that said sample can be substantially fully extracted without forming pockets of said sample isolated from said fitting.

16. The fluid sample bag improvement set forth in claim 15 wherein said passageway means comprises interconnected passageways between said opposed wall surfaces when said bag collapses.

17. The fluid sample bag improvement set forth in claim 16 wherein said passageways are arrayed in a grid.

18. The fluid sample bag improvement set forth in claim 17 wherein said passageway means maintains said opposed wall surfaces in spaced-apart relationship in a tent-like arrangement at said passageways when said opposed wall surfaces collapse into engagement with each other at locations in said grid between said passageways.

19. The fluid sample bag improvement set forth in claim 19 wherein said passageway means comprises a grid-like array of filamentary members arranged and disposed between said opposed surfaces to maintain said opposed walls spaced apart at said passageways.

20. In the method of taking a fluid sample with a sample bag of the type providing a sealable chamber formed by flexible sheet material impervious to fluids being sampled and a fitting wherein a fluid sample is introduced into said chamber through said fitting to expand said bag with opposed chamber surfaces moving away from each other, said chamber is sealed with said fluid sample therein and said chamber is subsequently unsealed to extract said sample with said opposed walls collapsing into engagement with each other, the improvement wherein while said bag is collapsing to bring said opposed surfaces into engagement with each other, the steps of maintaining said surfaces spaced apart in a predetermined pattern to provide passageways extending between said surfaces and establishing fluid communication from said fitting to substantially everywhere within said chamber while permitting said surfaces to collapse against each other at locations other than at said passageways so that said sample can be substantially fully extracted without forming pockets of said sample isolated from said fitting.

21. The method set forth in claim 20 wherein said wall surfaces are restrained from engaging with each other in a grid-like array of interconnected passageways.

22. The method as set forth in claim 21 wherein said passageways are formed by engaging a grid of filamentary members with said sheet material.

23. The method as set forth in claim 22 wherein said grid-like array is provided prior to filling said chamber with said sample by inserting a spacer in said chamber between said wall surfaces.

* * * * *